US009155562B2

(12) United States Patent  (10) Patent No.: US 9,155,562 B2
Cremer et al.  (45) Date of Patent: *Oct. 13, 2015

(54) FIXATION CLAMP

(71) Applicant: Stryker Trauma SA, Selzach (CH)

(72) Inventors: Axel Cremer, Lommiswil (CH); Beat Mürner, Reichenbach (CH); Umesh Verma, Delhi (IN); Usha Mathur, New Delhi (IN)

(73) Assignee: Stryker Trauma SA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,507

(22) Filed: Jul. 7, 2014

(65) Prior Publication Data

US 2014/0324045 A1  Oct. 30, 2014

Related U.S. Application Data

(63) Continuation of application No. 12/780,231, filed on May 14, 2010, now Pat. No. 8,827,997.

(30) Foreign Application Priority Data

May 15, 2009  (EP) .................................... 09160445

(51) Int. Cl.
*A61B 17/70*  (2006.01)
*A61B 17/64*  (2006.01)
(Continued)

(52) U.S. Cl.
CPC ........... *A61B 17/6466* (2013.01); *F16B 7/0493* (2013.01); *F16B 2/12* (2013.01)

(58) Field of Classification Search
CPC ............. A61B 17/6416; A61B 17/645; A61B 17/6458; A61B 17/6466; A61B 17/6475; A61B 17/6483; A61B 17/66; A61B 17/7049; A61B 17/705; A61B 17/7052; A61B 17/6425; A61B 17/6441; A61B 2019/267; F16B 7/044; F16B 7/0493; F16B 7/04; F16B 2/10; Y10T 403/7141; Y10T 403/7105; Y10T 403/7194; Y10T 403/7171; Y10T 403/7129
See application file for complete search history.

(56) References Cited

U.S. PATENT DOCUMENTS 24,303  A  *  6/1859  Herald ........................... 172/713
508,687  A  *  11/1893  Duggan ......................... 174/157
(Continued)

FOREIGN PATENT DOCUMENTS

CH  657899 A5  9/1986
DE  518329 C  2/1931
(Continued)

OTHER PUBLICATIONS

European Search Report, EP 09160445, dated Oct. 27, 2009.

*Primary Examiner* — Pedro Philogene
*Assistant Examiner* — Lynnsy Summitt
(74) *Attorney, Agent, or Firm* — Lerner, David, Littenberg, Krumholz & Mentlik, LLP

(57) ABSTRACT

A fixation clamp for use in an external fixation system for holding bone fragments adjacent to each other with the help of fixation elements has at least one clamping assembly having a pair of jaws with at least two different size grooves to accommodate a bone fixation element such as a pin or rod. An alternate clamping assembly has at least three grooves wherein at least two of the grooves have a different size adapted to accommodate a correspondingly sized bone fixation element such as a bone pin. The longitudinal axes of the grooves define a polygon. The jaw pairs can be rotated about a central longitudinal axis to present different size reception cavities towards the pins or rocks depending on their diameter.

20 Claims, 7 Drawing Sheets

(51) Int. Cl.
*F16B 7/04* (2006.01)
*F16B 2/12* (2006.01)

(56) References Cited

U.S. PATENT DOCUMENTS

| | | | | |
|---|---|---|---|---|
| 566,709 A * | 8/1896 | Bryan | | 403/256 |
| 693,206 A * | 2/1902 | Wyckoff | | 403/391 |
| 758,910 A * | 5/1904 | Grattelo | | 403/384 |
| 902,040 A * | 10/1908 | Wyckoff | | 403/391 |
| 944,850 A * | 12/1909 | Edmiston | | 24/135 R |
| 951,095 A * | 3/1910 | McCarthy | | 403/391 |
| 1,245,197 A * | 11/1917 | Crosby | | 403/394 |
| 1,950,635 A * | 3/1934 | Steinmayer | | 439/792 |
| 2,313,280 A * | 3/1943 | Szego | | 52/665 |
| 2,422,332 A * | 6/1947 | Becker | | 439/224 |
| 2,475,268 A * | 7/1949 | Wittle | | 81/438 |
| 2,658,776 A * | 11/1953 | Wilcox | | 52/653.2 |
| 2,683,329 A * | 7/1954 | Werner | | 446/122 |
| 2,696,996 A * | 12/1954 | Engelhardt | | 403/391 |
| 2,709,318 A * | 5/1955 | Benjamin | | 446/103 |
| 2,715,537 A * | 8/1955 | Hofheimer | | 403/173 |
| 2,745,181 A * | 5/1956 | Czerniewicz | | 33/27.03 |
| 4,589,236 A * | 5/1986 | McAllister | | 52/81.3 |
| 4,597,140 A * | 7/1986 | Girard | | 24/569 |
| 4,597,690 A * | 7/1986 | Girard | | 403/391 |
| 4,628,921 A * | 12/1986 | Rousso | | 606/54 |
| 4,653,481 A * | 3/1987 | Howland et al. | | 606/261 |
| 4,869,147 A * | 9/1989 | Hoshino | | 84/421 |
| 4,942,872 A * | 7/1990 | Jawish | | 606/57 |
| 4,958,793 A * | 9/1990 | Hess | | 248/125.9 |
| 4,978,347 A * | 12/1990 | Ilizarov | | 606/54 |
| 4,978,348 A * | 12/1990 | Ilizarov | | 606/57 |
| 4,982,546 A * | 1/1991 | Lange | | 52/655.1 |
| 5,030,220 A * | 7/1991 | Howland | | 606/261 |
| 5,127,759 A * | 7/1992 | Orbom | | 403/171 |
| 5,156,457 A * | 10/1992 | Dubach | | 362/431 |
| 5,304,177 A * | 4/1994 | Pennig | | 606/58 |
| 5,342,361 A * | 8/1994 | Yuan et al. | | 606/59 |
| 5,451,225 A * | 9/1995 | Ross et al. | | 606/59 |
| 5,451,226 A * | 9/1995 | Pfeil et al. | | 606/59 |
| 5,498,264 A * | 3/1996 | Schlapfer et al. | | 606/324 |
| 5,501,544 A * | 3/1996 | Cairns | | 403/400 |
| 5,540,686 A * | 7/1996 | Zippel et al. | | 606/56 |
| 5,584,833 A * | 12/1996 | Fournet-Fayard et al. | | 606/278 |
| 5,601,554 A * | 2/1997 | Howland et al. | | 606/252 |
| 5,624,440 A * | 4/1997 | Huebner | | 606/59 |
| 5,662,650 A * | 9/1997 | Bailey et al. | | 606/59 |
| 5,707,370 A * | 1/1998 | Berki et al. | | 606/59 |
| 5,728,096 A * | 3/1998 | Faccioli et al. | | 606/54 |
| 5,752,954 A | 5/1998 | Mata et al. | | |
| 5,810,817 A * | 9/1998 | Roussouly et al. | | 606/250 |
| 5,897,555 A * | 4/1999 | Clyburn et al. | | 606/54 |
| 5,961,515 A * | 10/1999 | Taylor et al. | | 606/59 |
| 6,022,348 A * | 2/2000 | Spitzer | | 606/54 |
| 6,059,784 A * | 5/2000 | Perusek | | 606/54 |
| 6,080,153 A | 6/2000 | Mata et al. | | |
| 6,273,633 B1 * | 8/2001 | Husson et al. | | 403/218 |
| 6,378,265 B1 * | 4/2002 | Konstandt | | 52/655.2 |
| 6,454,487 B1 * | 9/2002 | Buenning et al. | | 403/400 |
| 6,536,982 B2 * | 3/2003 | Gibbons et al. | | 403/97 |
| 6,565,564 B2 * | 5/2003 | Hoffman et al. | | 606/59 |
| 6,616,664 B2 * | 9/2003 | Walulik et al. | | 606/57 |
| 6,652,523 B1 * | 11/2003 | Evrard et al. | | 606/54 |
| 6,702,814 B2 * | 3/2004 | Walulik et al. | | 606/57 |
| 7,004,943 B2 * | 2/2006 | Ferrante et al. | | 606/59 |
| 7,241,074 B2 * | 7/2007 | Thomke et al. | | 403/385 |
| 7,491,008 B2 * | 2/2009 | Thomke et al. | | 403/373 |
| 7,527,626 B2 * | 5/2009 | Lutz et al. | | 606/54 |
| 7,588,571 B2 * | 9/2009 | Olsen | | 606/57 |
| 7,608,074 B2 * | 10/2009 | Austin et al. | | 606/54 |
| 7,618,417 B2 | 11/2009 | Thomke et al. | | |
| 2003/0187432 A1 * | 10/2003 | Johnson et al. | | 606/59 |
| 2004/0073212 A1 * | 4/2004 | Kim | | 606/56 |
| 2005/0228378 A1 * | 10/2005 | Kalfas et al. | | 606/61 |
| 2006/0235383 A1 * | 10/2006 | Hollawell | | 606/54 |
| 2006/0287652 A1 * | 12/2006 | Lessig et al. | | 606/54 |
| 2007/0038217 A1 * | 2/2007 | Brown et al. | | 606/57 |
| 2008/0016789 A1 * | 1/2008 | Boots | | 52/81.3 |
| 2008/0065068 A1 * | 3/2008 | Thomke et al. | | 606/57 |
| 2008/0215053 A1 * | 9/2008 | Thomke et al. | | 606/59 |
| 2008/0221571 A1 * | 9/2008 | Daluiski et al. | | 606/54 |
| 2008/0262545 A1 * | 10/2008 | Simonson | | 606/247 |
| 2009/0018541 A1 * | 1/2009 | Lavi | | 606/59 |
| 2009/0254086 A1 * | 10/2009 | Trilla-Muntanola | | 606/54 |
| 2009/0299368 A1 * | 12/2009 | Bauer | | 606/57 |
| 2009/0326532 A1 * | 12/2009 | Schulze | | 606/56 |
| 2010/0222778 A1 * | 9/2010 | Bagnasco et al. | | 606/58 |
| 2010/0262143 A1 * | 10/2010 | Bordeaux | | 606/54 |
| 2011/0087226 A1 * | 4/2011 | Murner et al. | | 606/54 |
| 2011/0112533 A1 * | 5/2011 | Venturini et al. | | 606/54 |
| 2011/0144643 A1 * | 6/2011 | Lorenz et al. | | 606/59 |
| 2012/0004659 A1 * | 1/2012 | Miller et al. | | 606/54 |

FOREIGN PATENT DOCUMENTS

| | | |
|---|---|---|
| DE | 10246418 A1 | 4/2004 |
| EP | 1820461 A1 | 8/2007 |
| JP | 2003325058 A | 11/2003 |

* cited by examiner

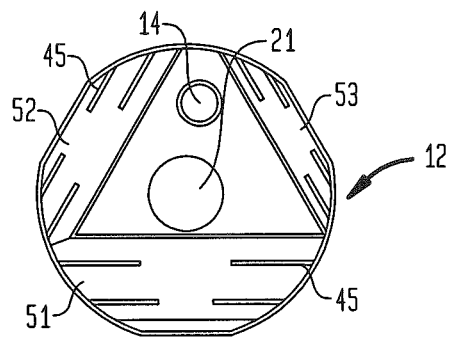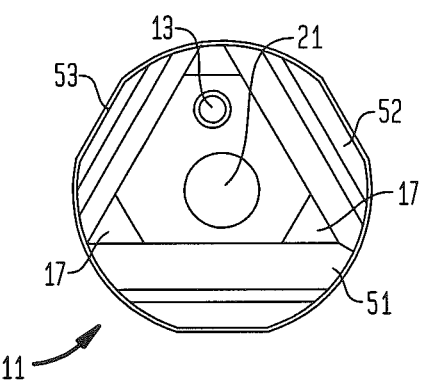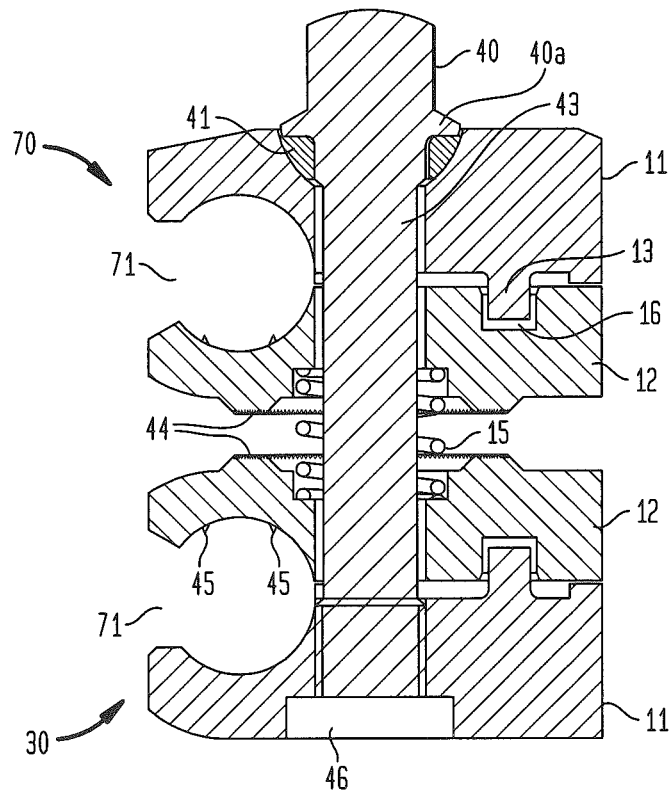

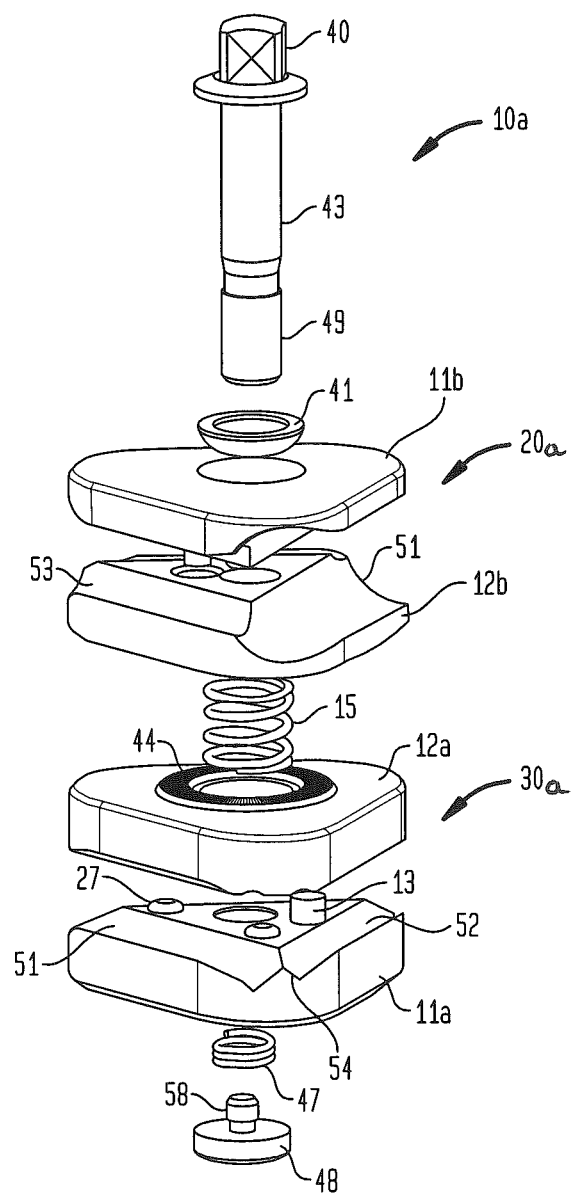

FIXATION CLAMP

CROSS REFERENCE TO RELATED APPLICATION

This application is a continuation of U.S. application Ser. No. 12/780,231, filed May 14, 2010, which claims the benefit of European Patent Application No. 09160445.4, filed May 15, 2009, entitled Fixation Clamp, the disclosures of which are hereby incorporated herein by reference.

BACKGROUND OF THE INVENTION

The present invention relates to a fixation clamp and, more particularly, to a fixation clamp for use in an external fixation system for holding bone fragments adjacent to each other.

External fixation systems are widely used to connect two or more bone fragments to each other. Such systems comprise bone screws, pins, wires which are inserted directly into the bone material and these systems use external structural elements as fixation rods, bars and rings. In order to connect the rods and bars to form a rigid frame, fixation clamps are used. Furthermore, fixation clamps are used to connect this screws and pins to the rigid frame to specifically hold bone fragments at an intended place.

One adjustable fixation clamp is known from U.S. Pat. Nos. 5,752,954 and 6,080,153, the disclosures of which are incorporated herein by reference, comprising two pairs of jaws allowing clamping of a rod as well as of a pin.

A clamp for multiple rod-shaped elements is known from U.S. Pat. No. 7,618,417, the disclosure of which is incorporated herein by reference, having one single pair of jaws. However, such a clamp allows clamping more than two, e.g. three or four rod-shaped elements such as pins with one single clamp, thus reducing the number of clamps. However, one further fixation clamp is necessary to fix the rod of said clamp to the frame of the fixation system.

U.S. Patent Publication No. 20060287652 discloses that the usual fixation clamps as e.g. known from U.S. Pat. No. 6,080,153 allow clamping of one single screw or pin to the frame and that this way to attach pins or rods leads to bulky fixation systems. Therefore U.S. Patent Publication No. 20060287652 discloses a fixation clamp addressing this problem and comprises two pairs of jaws within which each pair of jaws allows the introduction and clamping of two rods or pins etc. at the same time.

These clamps according to the prior art either provide different diameters of the reception cavities, such as grooves, provided by the jaws to introduce different sizes of rods, pins or wires, or they rely on additional inserts as e.g. disclosed in U.S. Patent Publication No. 20080065068. Such inserts reduce the diameter of the reception cavities to allow a secure fixing of differently sized rods, pins or wires.

BRIEF SUMMARY OF THE INVENTION

Solutions according to the prior art providing different diameter reception cavities necessitate provision of either a variety of different clamps or additional inserts.

It is one aspect of the invention to overcome this problem and to provide the practitioner with a fixation clamp, especially for use in an external fixation system, which clamp can directly be used with a variety of differently sized rods, pins, screws and wires.

A fixation clamp for use in an external fixation system for holding bone fragments adjacent to each other with the help of fixation elements includes at least one clamping assembly, and a central locking shaft extending through the one or more clamping assemblies for blocking the position of the clamping assemblies in a defined angular position; wherein each clamping assembly comprises two jaws, wherein each jaw comprises three grooves. The longitudinal axis of each groove is perpendicular to the locking shaft. One groove of one jaw corresponds to one groove of the other jaw to form a cavity to accommodate a bone fixation element. The longitudinal axes of the grooves may span a triangle, and wherein at least two grooves have a different size adapted to accommodate a correspondingly sized fixation element. The fixation clamp groove may have a different size. The fixation clamp for use in an external fixation system for holding bone fragments adjacent to each other with the help of fixation elements also may include at least one clamping assembly having jaws mounted on a locking shaft, each jaw having four grooves forming a cavity to accommodate a bone fixation element along the longitudinal axis of the groove. The longitudinal axes of these grooves form a quadrilateral. At least two grooves have a different size adapted to accommodate a correspondingly sized fixation element. Each groove of the fixation clamp has a different size wherein two opposite grooves have the same size. The fixation clamp for use in an external fixation system for holding bone fragments adjacent to each other with the help of fixation elements may have at least one clamping assembly including at least one pair of jaws mounted on a locking shaft having five grooves to accommodate a bone fixation element along the longitudinal axis of the grooves. The longitudinal axes of the grooves form a pentagon, and in that at least two grooves have a different size adapted to form a cavity to accommodate a correspondingly sized fixation element. Each groove set forms a different size cavity. The grooves of all clamping elements may be circular or triangular in crossection and may comprise longitudinal ribs. Each clamping assembly preferably comprises an anti-rotation pin extending from a first jaw into a complementary recess in an opposite jaw. The grooves may be provided within outer side walls of each jaw in a way that the surface of a fixation element pointing away from the locking shaft when inserted into one groove is flush with the corresponding side wall.

A fixation clamp for use in an external fixation system for holding bone fragments adjacent to each other with the help of fixation elements includes a first and a second jaw member. A central locking shaft extends through the first and second jaw members wherein each jaw member comprises at least three grooves. The longitudinal axis of each groove lies in a plane perpendicular to a longitudinal axis of the locking shaft. One groove of the first jaw member corresponds to one groove of the second jaw member to form a cavity to accommodate a bone fixation element. The longitudinal axes of the grooves are all non-parallel in the plane. The first and second jaw members have a face parallel to the plane containing the longitudinal axis of the at least three grooves. An anti-rotation pin extends perpendicular to the plane of the face of the first jaw extends into a bore in the planar face of the second jaw member. The pin and bore are located within a geometric shape formed by the grooves. The fixation clamp for use in an external fixation system for holding bone fragments adjacent to each other with the help of fixation elements may have first and second jaw members having four grooves to accommodate a fixation element along the longitudinal axis of the groove wherein the longitudinal axes of said grooves form a quadrilateral. At least two grooves have a different size adapted to accommodate a correspondingly sized fixation element.

The fixation clamp for use in an external fixation system for holding bone fragments adjacent to each other with the help of fixation elements may include first and second jaw members having five grooves to accommodate a fixation element along the longitudinal axis of the grooves. The longitudinal axes of the grooves form a pentagon, and in that at least two grooves have a different size adapted to form a cavity to accommodate a correspondingly sized fixation element.

The clamp according to the invention allows readily treating different types of fractures or connecting bones of different sizes to each other, since usually different pin diameters are required. The clamp provides a plurality of different couplings possibilities which is an advantage, avoiding mismatching of components, which can lead to insufficient connecting strength. The clamp according to the invention also allows for clicking in rods from the side. The clamp can be built based on the usual metallic components and can comprise non-magnetic and non conductive materials, which are safe for temporary exposition in a MRI scanner, and can furthermore comprise plastic or composite materials or have electrical insulating cover surfaces.

It is an advantage of the clamp according to the invention that after having clamped a bone screw with one clamping assembly, a practitioner attaching subsequently a rod of an external fixator to the other clamping assembly can check the robustness of the external fixator, and if the practitioner finds that the rod used is not stiff enough, one simply opens the other clamping assembly, removes the thinner rod, turns the other clamping assembly e.g. 60 degrees into one direction or the other around the longitudinal axis to align a larger reception cavity with the new thicker rod and replaces said rod. This change does not necessitate the replacement of the clamp itself and is thus faster and more reliable since the clamping of the bone screw is not changed, and the use of a second sterile clamp at said time is avoided.

BRIEF DESCRIPTION OF THE DRAWINGS

Preferred embodiments of the invention are described in the following description with reference to the drawings, which are provided for the purpose of illustrating the present preferred embodiments of the invention and not for the purpose of limiting the same. In the drawings.

FIG. 5 is a top view of an inner jaw portion of the clamp according to FIG. 1;

FIG. 6 is a top view of an outer jaw portion of the clamp according to FIG. 1;

FIG. 7 is a cross-section of the clamp shown in FIG. 4;

FIG. 8 is an exploded view of a second embodiment of the clamp of the present invention;

DETAILED DESCRIPTION

Figure 1:
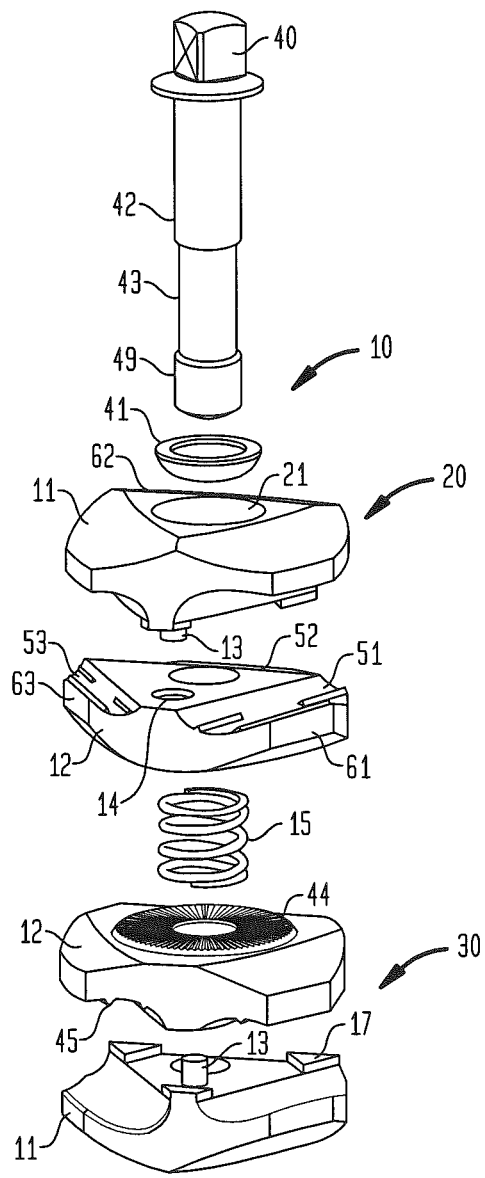
FIG. 1 is an exploded view of a first embodiment of the clamp of the present invention.

Referring to FIG. 1 there is shown a perspective exploded view of a preferred first embodiment of a clamp 10 pursuant to the invention. The clamp 10 consists of a first clamping assembly 20 and a second clamping assembly 30 and a shaft 40 which is positioned through bores 21, 31 within the two clamp assemblies 20, 30 along the longitudinal axis of shaft 40. Each clamping assembly has a first jaw 11 and a second jaw 12. Shaft 40 is preferably a locking element adapted to allow the closing the clamp assemblies 20 and 30. Shaft 40 enters a first jaw 11 through a washer 41. Washer 41 may have a part-spherical shape for receipt on a part-spherical surface of bore 21. The shaft 40 comprises a proximal portion 42 and a reduced diameter portion 43 which is followed by a threaded portion 49. The outer threaded portion 49 is adapted to be screwed into a complementary inner thread which may be formed within the distal most jaw 11 (bottom jaw of FIG. 1) so that turning the head of the shaft 40 changes the longitudinal position of the shaft 40 against the bottom jaw 11. This allows for opening or closing the entire clamp 10 against the force of a spring 15 provided between the two clamp assemblies 20 and 30. Obviously a separate nut could be provided rather than threading the bore in lowermost jaw 11 of FIG. 1. Spring 15 is preferably positioned in corresponding reception cavities in jaws 12. Instead of a spring 15, provided around shaft 40, it is possible to provide a different spring means as Belleville washers or an elastic compressible solid or foam. Upon closing of the clamp assemblies 20 and 30 the jaws 12 adjacent spring 15 can eventually come into contact and then the anti-rotation surface 44 which is provided in both surfaces of the jaws, fixes the angular orientation of each clamping assembly 20 and 30 against each other.

Preferably after having mounted the shaft 40 with the thread 49 within the bottom jaw 11, the end portion of the thread 49 is deformed or destroyed through pressure to ensure that the shaft 40 cannot be removed from the clamping assemblies 20, 30 to maintain the clamp as one single piece.

As discussed above, each clamping assembly 20 or 30 comprises two opposing clamping jaws 11 and 12. These jaws 11 and 12 are essentially similarly shaped on the sides facing each other except for a pin 13 which extends into a corresponding bore 14 in clamping jaw 12. This pin-bore connection which is oriented along or parallel to the longitudinal axis of the clamping device is an anti-rotation device for jaws 11 and 12. Once engaged jaws 11, 12 cannot change their mutual angular orientation. The plane surface of jaw 11 facing the plane surface of jaw 12 is provided with three spacers 17 arranged in the corners of the surface. The spacers 17 have a mostly triangular form and a height to allow the function of a counter bearing as explained below. Additionally, the spacers 17 result in the two plane surfaces of jaws 11 and 12 being spaced so that the open areas between these surfaces can be cleaned.

The jaws 11 and 12 are provided with three grooves 51, 52 and 53. Grooves 51, 52 and 53 are all provided in a same plane perpendicular to the longitudinal axis of shaft 40. In that plane they are oriented perpendicular to the radial direction from the center of the bore 21 or 31. As such the grooves 51, 52 and 53 are parallel to outer side wall 61, 62 or 63 of each pair of triangularly shaped jaws 11 and 12.

Each pair of grooves 51, 52 or 53, respectively, in each jaw 11 and 12, define one reception cavity, i.e. a first reception cavity 71, a second reception cavity 72 and a third reception cavity 73. The grooves 51, 52 and 53 are each formed as a rounded semi-spherical recess in section to provide reception cavities 71, 72 and 73 which accommodate cylindrical pins or rods 100 with a defined diameter (see FIGS. 11 to 13), if the clamp is closed. The outer side walls 61, 62 or 63 can comprise an inclined sliding surface to allow for easy clipping or snapping in of such pins or rods 100 into the corresponding cavities. The grooves 51, 52, 53 are formed as rounded semi-spherical recesses in a section. This means that the recesses provided by the grooves 51, 52, 53 have a hollow cylindrical shape to accommodate rod-shaped elements.

All three grooves 51, 52 and 53 have different sizes so that the corresponding reception cavities 71, 72 and 73 have three different sizes. In other words each reception cavities 71, 72 or 73 is adapted to accept a different fixation element, i.e. a rod, screw, pin or wire having a different diameter. One preferred embodiment of the first clamping assembly 20 has grooves to accept fixation elements having a diameter of 12 mm, 8 mm and 5 mm, respectively. A different embodiment may have a sequence of diameters of 8 mm, 6 mm and 4 mm, respectively.

The second clamping assembly 30 according to the embodiment of FIG. 1 also comprises two jaw portions 11 and 12 and these comprise three grooves 51, 52, 53. These grooves 51, 52, 53 also comprise a sequence of different sizes. In the embodiment shown the inner jaws portion 12 have an identical structure as have the outer jaws 11, especially in view of the anti-rotation device 44, the second bore for a spring 15 as well as ribs 45 inside the grooves 51, 52, and 53.

Within a preferred embodiment the first clamping assembly 20 may comprise a sequence of smaller size cavities, e.g. 7 mm, 5 mm and 3 mm; or 6 mm, 5 mm and 4 mm; and the second clamping assembly 30 may comprise a sequence of larger sizes, e.g. 13.5 mm, 12 mm and 10 mm. Different sizes are possible, usually for wires starting from 2 mm diameter up to thicker rods with a diameter of 30 mm are used within such a clamp 10. Such a clamp 10 allows the use of one single versatile clamp, wherein the first clamping assembly 20 is used to fix a specific pin or screw or wire having a diameter for which one of the reception cavities 71, 72 or 73 is adapted. The user takes the clamp 10 and orients or rotates the first clamping assembly 20 into the correct alignment so that the pin or screw can be clipped into the corresponding reception cavity.

Then the clamp 10 can be clamped on a rod of an external fixator with the help of the second clamping assembly 30. The second clamping assembly 30 can be oriented in a way so that the rod can be clipped into the corresponding reception cavity. It is an advantage of the clamp 10 having two clamping assemblies 20 and 30 according to the invention, that a practitioner attaching such a clamp at a bone screw with one clamping assembly 20 and subsequently a rod of an external fixator to the other clamping assembly 30 can check the robustness of his external fixator, and if it is found that the rod used is not stiff enough, one simply opens the second clamping assembly 30, removes the thinner rod, turns the second clamping assembly 30 e.g. 60 degrees in one direction or the other around the longitudinal axis, to align the larger reception cavity with the new thicker rod and replaces it. This change does not necessitate the replacement of the clamp 10 itself as necessary with prior art systems. The method to replace such a rod 100 is faster and more reliable since the clamping of the bone screw is not changed, and at the same time avoids use of a second sterile clamp.

It is of course also possible that the second clamping assembly 30 is a traditional clamping assembly or even any other element known in the prior art with clamping elements. The object of a versatile clamping assembly is already achieved through one first clamping assembly 20, since it allows clamping one of three different sizes of screws, pins of wires through simple reorientation of the first clamping assembly 20.

Figure 2:
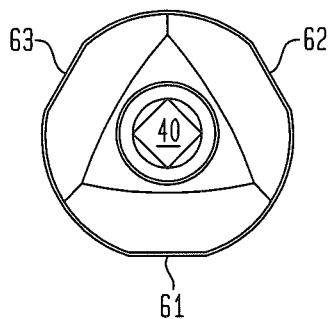
FIG. 2 is a top view of the clamp according to FIG. 1.

FIG. 2 shows a top view of the clamp according to FIG. 1. Since the embodiment of FIG. 1 comprises three grooves 51, 52 and 53, there are three side walls 61, 62 and 63, which provide, when looked from above as in FIG. 2 a triangular shape of each clamping assembly 20 or 30.

Figure 3:
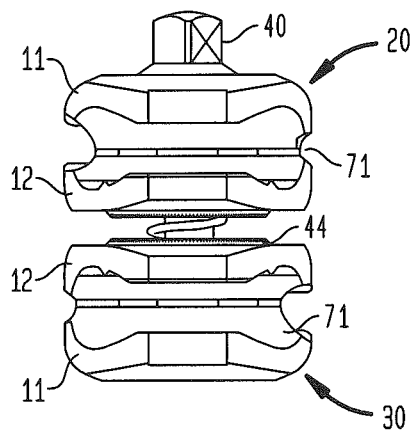
FIG. 3 is a first side view of the assembled clamp of FIG. 1.
Figure 4:
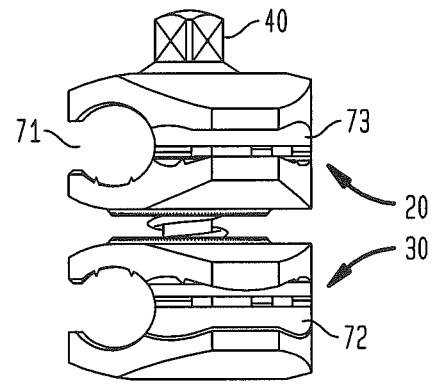
FIG. 4 is a second side view of the assembled clamp of FIG. 1 from a different direction than FIG. 3.

FIG. 3 shows a first side view of the clamp of FIG. 1 and FIG. 4 shows a second different side view of the clamp 10 of FIG. 1 from a different direction. Identical reference signs are used for identical features within the same embodiment and are used for identical or similar features in further embodiments.

It is clear from FIG. 3 that the first reception cavity 71 is identical in size and allows for insertion of a large rod. From FIG. 4 it can be seen that the third reception cavity 73 are small cavities, e.g. for a pin. In this embodiment, second cavities 72 have an intermediate size. From FIG. 4 it can be seen that the depicted embodiment has a decreasing size sequence of reception cavities 71, 72 and 73 in the upper first clamping assembly 20 in clockwise direction whereas the depicted embodiment has a decreasing size sequence of the reception cavities 71, 72 and 73 in the lower second clamping assembly 30 in counter-clockwise direction.

Referring to FIG. 5 there is shown a top view of an inner jaw portion 12, whereas FIG. 6 shows a similar view on a corresponding outer jaw portion 11. It is clear that each jaw portion 11 or 12 of any clamping assembly 20, 30 according to the invention comprises three differently sized grooves 51, 52 and 53, respectively. The longitudinal axes of these grooves 51, 52 and 53 are oriented in an angle of 60 degree one to another. However, these angles of 60 degree are not mandatory. It is only necessary that the total internal angle of the triangle provided by these three grooves 51, 52 and 53 is 180 degrees. The grooves are also in the same median plane which indicates that only one pin, screw or rod can usually be introduced in one of the grooves 51, 52 or 53 and such an introduction blocks the other empty grooves. It is an aim of this orientation to provide a simpler mounting of a fixation device, since based on the chosen pin or screw a clamp of the invention can be chosen and through rotation of the clamping assembly the correct sized reception cavities 71, 72 or 73 is usable for a well clamped connection, wherein the clipping of the pin or screw from the open side further facilitates their introduction.

It is clear from FIGS. 5 and 6 that the grooves 51, 52 and 53 mutually intersect. The inner jaw portion 12 shown in FIG. 5 comprises ribs 45 which are oriented in the longitudinal direction of the grooves 51, 52 and 53. Each groove is provided with two lines of ribs 45, which are arranged one behind the other and thus can also be described to be a single line interrupted in the middle part. Of course there may be one or no ribs 45, or there may be more than two lines, and these lines can be provided uninterrupted, although the embodiment with interrupted ribs 45 as well as two lines of these ribs 45 is preferred.

It is possible to deviate from the correct triangular orientation of the grooves; especially the angle between the largest groove 51 and the neighboring grooves can be less than 60 degree, so that the angle between the longitudinal axes of the grooves 52 and 53 is greater then 60 degrees.

It is also possible, in different embodiments, not shown in the figures, to provide four, five or more grooves. If four grooves are provided, then the form of such a clamping assembly 20 seen from above is a square and each jaw comprises four grooves joining in the corners in at preferably a right angle. Then a sequence of four sizes of the reception cavities is possible as 12 mm, 8 mm, 6 mm and 4 mm. If five grooves are provided, then the form of such a clamping assembly 20 seen from above is a pentagon and each jaw comprises five grooves joining in the corners, preferably at an angle of around 108 degrees. Then a sequence of five sizes of the reception cavities is possible as 12 mm, 20 mm, 8 mm, 6 mm and 4 mm. Of course deviations from such a symmetrical polygon are possible.

It is noted that the spacers 17 and thus the counter bearings as well as the corners of the jaw planes are not symmetrically positioned in view of the central bore 21 of a jaw. The deviation from the symmetric form is smaller for the largest reception cavity 71 and larger for the smallest reception cavity 73. However, this is not problematic, since the largest reception cavity 71 with the smallest deviation accepts the largest rod and thus the largest forces, wherein the largest deviation occurs for the smallest reception cavity and the function of such a small reception cavity resides in accepting a limited force.

FIG. 7 shows a cross-section of the clamp according to FIG. 4, wherein the clamp 10 is shown in a premounted state, i.e. the spring 15 is under tension. The upper jaw 11 of the first clamping assembly 20 is therefore pushing the rounded counter piece 41 against a flange 40a of the head of shaft 40. The jaw 11 has around its bore 21a rounded part-spherical recess to accommodate the washer 41. This enables a pivoting movement of the upper jaw 11 against the axis of the shaft 40, since the shaft 40 comprises a reduced diameter portion 43 extending over the whole length of the jaws 11 and 12 in both assemblies. It is also possible that there is no play between shaft 40 and jaw 11; the bore 21 just allows the introduction of the shaft 40. Then jaw 11 and jaw 12 can only effect a translatory movement.

The pin 13 of the upper jaw 11 is lodged in a recess 16 in the bore 14. It is possible but not necessary that the pin 13 or the recess 16 receives an elastic fitting piece allowing elastic movements of the pin within the recess 16.

The shaft 40 as part of a locking element is threaded into the lower jaw 11 of the second clamping assembly 30 and is further connected with a counter nut 46, which is fixedly lodged on shaft 40. Therefore the two clamp assemblies 20, 30 can be opened and closed through turning the head of shaft 40 and thus turning shaft 40 with the blocking counter nut 46 and in the jaw thread. The counter nut 46 can then be used to lock shaft 40 from further rotation The combination of shaft 40 and counter nut 46 can also be replaced by a single screw to be screwed into the lower jaw 11 of the second clamping assembly 30. Threading may be provided in the bore or the screw may exhibit self-tapping threading. Quite generally, a locking element may be provided which may be a lever locking element or a bayonet lock. Among these locking elements may also be supporting disks or toothed disks, which, for the sake of simplicity, are not shown in the drawings.

Figure 9:
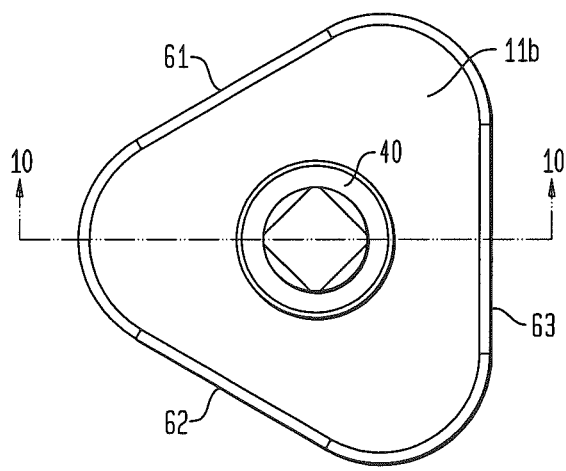
FIG. 9 is a top view of the clamp shown in FIG. 8.
Figure 10:
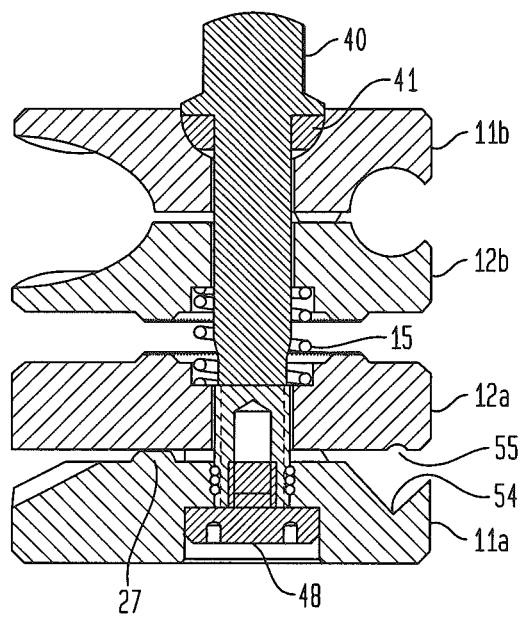
FIG. 10 is a cross-section of the clamp of FIG. 8 along line X-X of FIG. 9.

FIG. 8 shows an exploded view of a second embodiment of a clamp 10a of the present invention; FIG. 9 shows a top view of the clamp and FIG. 10 shows a cross-section of the clamp along line X-X in FIG. 9. The sequence of sizes for the first clamping assembly 20a is 13.5 mm, 8 mm and 5 mm. The choice of this sequence depends on the intended application (e.g. which limb is to be treated) of the external fixator set and follows the needs of the application.

The clamping assemblies 20a, 30a of the embodiment have a triangular form, as can be seen from FIG. 9, having defined straight side walls 61, 62 and 63 and identically curved transitory portions. For a description of features which are identical to the clamp of FIG. 1 reference is made to that description.

Instead of spacers 17 in the corners of the plane surface of the jaws 11a there are provided two flattened semi-spherical spacers 27 on the surface. As mentioned above, the first clamping assembly 20a comprises a sequence of larger sized reception cavities 71, 72, 73. The lower second clamping assembly 30 comprises a different sequence of smaller sized reception cavities 71, 72, 73. The corresponding grooves 51, 52 and 53 within the lower jaw 11a are not semi-spherical as with the clamp of FIG. 1 but are triangular or v-shaped grooves 51, 52, 53 having a bottom line 54 of a v-shaped groove. The corresponding groove portion in the opposite jaw 12a is a rounded groove, in FIG. 10 receiving the numeral 55, so that slightly different sizes of elements can be clamped. However, the sizes of the grooves 51, 52 and 53 are nevertheless different one from the other.

Usually the rounded grooves are intended to be used especially with carbon rods and allow high precision clamping under all circumstances, whereas the triangular grooves are more flexible. They usually provide two sizes with one groove, e.g. 4-5 mm, 5-6 mm and 7-8 mm for three grooves.

Element 47 is a steel helicoil inserted into an aluminum jaw 11a to provide a better counter thread for the thread 49 of shaft 40. The end portion 49 of shaft 40 is hollow with an additional inner thread to accommodate the outer thread 58 of a counter nut 48.

Figure 11:
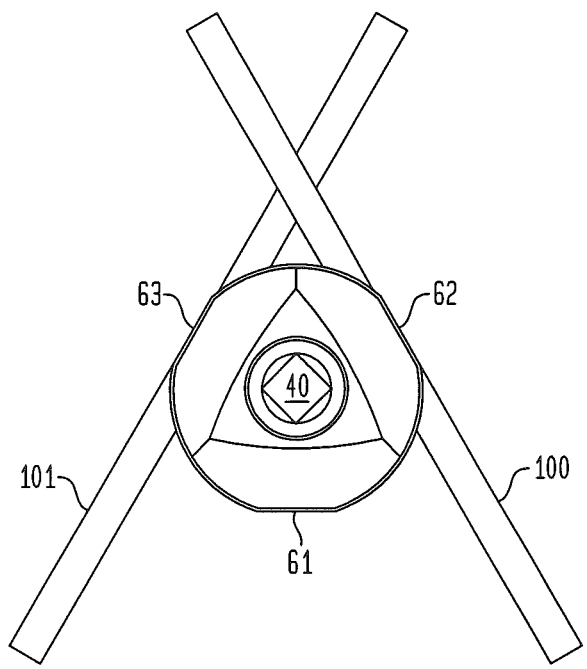
FIG. 11 is a top view of the clamp of the present invention with two attached fixation elements.
Figure 12:
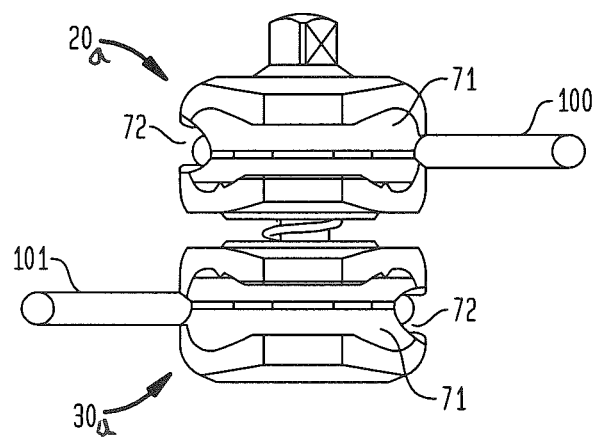
FIG. 12 is a front view of the clamp with two attached fixation elements according to FIG. 11.
Figure 13:
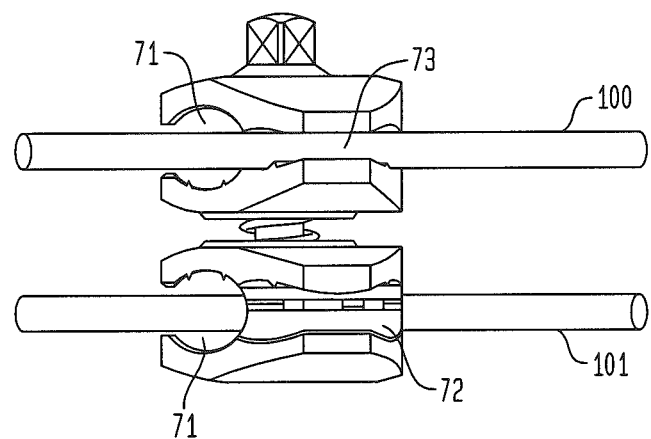
FIG. 13 is a right side view of the clamp of FIG. 11 with two attached fixation elements.

FIG. 11 shows a top view of the clamp 10a of the present invention with two attached fixation elements 100 and 101. FIG. 12 shows a front view of the clamp according to FIG. 11; and FIG. 13 shows a view from the right.

The fixation elements shown here are small-sized rods. Fixation element 100 is introduced in the smallest size reception cavity 73 of the first clamping assembly 20 leaving the middle-sized reception cavity 72 and the large-size reception cavity 71 empty. From FIG. 12 it can be seen that the introduction of rod 100 blocks the section of reception cavity 72. From FIG. 13 it can be seen that the introduction of rod 100 also blocks the section of reception cavity 73. Therefore a clamping assembly 20 is usable for one single rod or pin at the same time, here rod 100.

The same is true for rod 101 used in connection with the second clamping assembly 30a. In this embodiment, the two clamping assemblies have an identical sequence of reception cavity sizes, i.e. there are three sizes of reception cavities twice in the clamp 10a. As mentioned above it is possible to provide different reception cavity sizes in the two clamping assemblies 20, 20a and 30, 30a. Therefore it is possible to have up to six different sizes of reception cavities within one clamp consisting of two clamping assemblies according to the invention, e.g. 3 mm, 4 mm, 5 mm, 6 mm, 8 mm, and 10 mm. It has to be noted that the sequence is not necessarily distributed according to size. One clamping assembly can have sizes 3 mm, 5 mm and 8 mm, whereas the complementary assembly has the sizes 4 mm, 6 mm and 10 mm, showing a mixed sequence.

It is also possible to use two rods 100 and 101 with one single clamping assembly 20, 20a, if the rods are shorter so that the rods 100, 101 cannot intersect behind the clamp 10. This allows providing a so-called Y-frame with one single clamping assembly, wherein the two rods or bone screws are oriented within an angle of 60 degrees.

It is noted that the grooves 51, 52 and 53 are preferably provided at a distance from the center of the clamp 10 so that the rods, pins or screws which are to be inserted in the created reception cavities are flush with the side walls 61, 62 or 63 as it can be seen in FIG. 11.

The single clamping assemblies 20, 20a or 30, 30a can be combined in different ways. If a clamping assembly having round grooves is called a rod clamping assembly and a clamping assembly having triangular grooves is called a pin clamping assembly then several clamps having two single clamping assemblies 20, 20a or 30. 30a are possible, i.e. pin-pin, rod-pin or rod-rod.

The clamp or articulation element according to the invention has at least two opposing first and second clamping jaws 11, 11a and 12, 12a, providing one lateral open free space for laterally receiving a rod-shaped element 100. The lateral open free space is formed through grooves and is in the form of an open slot. It is also possible to accommodate inserts, i.e. a jacket element adapted to be inserted in one jaw of the clamp to modify the space available for the rod-shaped element. Such an insert can be built according to e.g. U.S. Patent Publication No. 20080065068 and introduced into the reception cavities to have additional versatility. On the other side it is also possible that a triangular clamp 10, 10a according to the invention comprises a clamping assembly 20, 20a or 30, 30a having two identical grooves within the three grooves. This is especially true, if according to a different embodiment, four, five or more grooves are provided.

For four grooves it is possible to combine the advantage of using two sizes of reception cavities which are provided one opposite to the other. Then—in clockwise direction—the four cavities may be: small, large, small, large; which allows the parallel introduction and fixation of two small pins or two large rods, since the square disposition do not hinder the simultaneous introduction of two pins or rods. The same is true, if five grooves/reception cavities are provided, since an angle of around 108 degrees, two out of the five reception cavities can be used.

Within a preferred embodiment it is contemplated that at least the lower jaw 11, 11a of the second assembly 30, 30a has a different color then the other jaws to indicate that there is a specific sequence of sizes. It is e.g. possible that said lower jaw is green, indicating that said clamping assembly 30, 30a provides a sequence of larger reception cavities (13.5 mm, 10 mm, 8 mm) whereas the other clamping assembly 20, 20a provide smaller reception cavities (e.g. 6 mm, 5 mm and 4 mm). It is also possible to provide the upper most jaw 11, 11a of the first clamping assembly 20, 20a with a different color, e.g. blue to indicate that said clamping assembly 20 provides the smaller reception cavities. Then of course, blue-blue, blue-green and green-green combinations of clamps 10, 10a would provide a high usability of use with direct indication for the user, which clamp he should choose. This color model can be extended to a third of fourth color according to the above mentioned sequences of reception cavity sizes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation clamp for use in an external fixation system for holding bone fragments adjacent to each other with the help of fixation elements, comprising:
   at least one clamping assembly;
   a central locking shaft extending through the at least one clamping assembly for blocking a position of the at least one clamping assembly in a defined angular position; and
   wherein the at least one clamping assembly comprises first and second jaws, the first and second jaws define outer side surfaces wherein each first and second jaw comprises three and only three grooves, wherein the longitudinal axis of each groove lies in a plane that is perpendicular to the central locking shaft, wherein one groove of the first jaw corresponds to one groove of the second jaw to form a recess to accommodate a fixation element, wherein the longitudinal axes of the grooves on the first and second jaws span a triangle, and wherein the three grooves in the first and second jaws each have a different cross-sectional size adapted to accommodate three correspondingly different size fixation elements, wherein the longitudinal axis of each groove in the first and second jaws intersects the longitudinal axis of each of the other two grooves forming three angles totaling 180°.

2. The fixation clamp according to claim 1, wherein the grooves either in the first and second jaws are circular or triangular in cross section.

3. The fixation clamp according to claim 1, wherein the grooves in the first and second jaws further comprise longitudinal ribs.

4. The fixation clamp according to claim 1, wherein the at least one clamping assembly comprises an anti-rotation element extending outwardly from the first jaw into a complementary recess in the second jaw.

5. The fixation clamp according to claim 1, wherein the grooves in the first and second jaws are provided within the outer side surface of the corresponding jaw and spaced from the central locking shaft so that an outer surface of a fixation element pointing away from the locking shaft when inserted into one groove is flush with the corresponding outer side surface.

6. A fixation clamp for use in an external fixation system for holding bone fragments adjacent to each other with the help of fixation elements, comprising at least one clamping assembly having first and second jaws mounted on a locking shaft, each jaw defining an outer side surface and having three and only three grooves to accommodate a fixation element along the longitudinal axis of each groove in the first or second jaws, wherein the longitudinal axes of said grooves form a triangle, and in that at least two grooves have a different cross-sectional size adapted to accommodate a correspondingly sized fixation element wherein the triangle has three angles with each angle being 60°.

7. The fixation clamp according to claim 6, wherein each of the three grooves in the first and second jaws has a different size.

8. The fixation clamp according to claim 6, wherein the grooves in the first or second jaws are either circular or triangular in cross section.

9. The fixation clamp according to claim 6, wherein the grooves in the first and second jaws further comprise longitudinal ribs.

10. The fixation clamp according to claim 6, wherein the at least one clamping assembly comprises an anti-rotation pin extending from the first jaw into a complementary recess in the second jaw.

11. The fixation clamp according to claim 6, wherein the grooves in the first and second jaw are provided within the outer side surface of the corresponding jaw in a way that an outer surface of a fixation element pointing away from the locking shaft when inserted into one groove is flush with the corresponding outer side surface.

12. The fixation clamp according to claim 6, wherein two facing grooves on the first and second jaws have the same size.

13. The fixation clamp as set forth in claim 6 wherein the three angles totaling 180° are each 60°.

14. A fixation clamp for use in an external fixation system for holding bone fragments adjacent to each other with the help of fixation elements, comprising: at least one clamping assembly including first and second jaws mounted on a locking shaft, the first and second jaws each having outer side surfaces and three and only three grooves to accommodate a fixation element along the longitudinal axis of the grooves, wherein the longitudinal axes of the grooves form a triangle, and in that the three grooves of the first and second jaws all have a different cross-sectional size adapted to accommodate three correspondingly different size fixation elements, the three grooves on the first and second jaws each lying in a plane perpendicular to a longitudinal axis of the locking shaft and are oriented at 60° angles to one another;

wherein a bore in each jaw for receiving the locking shaft is located closer to the groove with the largest cross-sectional size.

15. The fixation clamp according to claim 14, wherein the grooves in the first and second jaws are either circular or triangular in cross section.

16. The fixation clamp according to claim 14, wherein the grooves in the first and second jaws comprise longitudinal ribs.

17. The fixation clamp according to claim 14, wherein the at least one clamping assembly comprises an anti-rotation pin extending from the first jaw into a complementary recess in the second jaw.

18. The fixation clamp according to claim 14, wherein the grooves in the first and second jaws are provided within the outer side surfaces of the corresponding jaw and spaced from the locking shaft such that an outer surface of a fixation element pointing away from the locking shaft when inserted into one groove is flush with the corresponding jaw outer side surface.

19. A fixation clamp for use in an external fixation system for holding bone fragments adjacent to each other with the help of fixation elements, comprising:

a first and a second jaw member, each jaw member having a surface facing the other jaw;

a central locking shaft extending through the first and second jaw members along a longitudinal axis;

wherein the facing surfaces each of the first and second jaw members comprise three and only three grooves, at least two grooves on each jaw member having a different cross-sectional size, wherein the longitudinal axis of each groove in the first and second jaw members lies in a plane perpendicular to the longitudinal axis of the locking shaft, wherein one groove of the first jaw member corresponds to one groove of the second jaw member to form a cavity to accommodate a fixation element, wherein the longitudinal axes of the three grooves on the first and second jaw members form a triangle in the plane, wherein the first and second jaw members have a planar face parallel to the plane containing the longitudinal axes of the three grooves, an anti-rotation element extending outwardly of the plane of the face of the first jaw extends into a recess in the planar face of the second jaw member, the anti-rotation element and recess located within the triangle formed by the grooves, the longitudinal axes of the three grooves forming three angles totaling 180°, wherein a portion of the facing surface of one jaw located between the three grooves and the central locking shaft is spaced outwardly from a remaining portion of the facing surfaces to space the remaining portion of the facing surfaces apart.

20. The fixation clamp as set forth in claim 19 wherein the three angles totaling 180° are each 60°.

\* \* \* \* \*